(12) United States Patent
Beckman

(10) Patent No.: US 9,778,003 B2
(45) Date of Patent: Oct. 3, 2017

(54) PROJECTILES SPECIALIZED FOR DNA AND OTHER TRACE EVIDENCE COLLECTION

(71) Applicant: Christopher V. Beckman, San Diego, CA (US)

(72) Inventor: Christopher V. Beckman, San Diego, CA (US)

( * ) Notice: Subject to any disclaimer, the term of this patent is extended or adjusted under 35 U.S.C. 154(b) by 0 days.

(21) Appl. No.: 15/245,165

(22) Filed: Aug. 23, 2016

(65) Prior Publication Data

US 2016/0356582 A1    Dec. 8, 2016

Related U.S. Application Data

(63) Continuation-in-part of application No. 14/828,514, filed on Aug. 17, 2015, now Pat. No. 9,423,223, which is a continuation-in-part of application No. 13/666,965, filed on Nov. 2, 2012, now Pat. No. 9,109,864.

(51) Int. Cl.
| | |
|---|---|
| *F42B 12/02* | (2006.01) |
| *A61B 10/00* | (2006.01) |
| *F42B 12/36* | (2006.01) |
| *F42B 12/52* | (2006.01) |
| *F42B 15/01* | (2006.01) |

(52) U.S. Cl.
CPC .......... *F42B 12/02* (2013.01); *A61B 10/0045* (2013.01); *F42B 12/36* (2013.01); *F42B 12/52* (2013.01); *F42B 15/01* (2013.01)

(58) Field of Classification Search
CPC .......... F42B 12/40; F42B 12/02; F42B 12/36; F42B 12/52; F42B 15/01; A61B 10/0045

USPC ................................ 102/481, 293, 502, 513
See application file for complete search history.

(56) References Cited

U.S. PATENT DOCUMENTS

| | | | | |
|---|---|---|---|---|
| 4,517,978 | A * | 5/1985 | Levin | A61B 5/150022 604/136 |
| 5,324,303 | A * | 6/1994 | Strong | A61B 5/150022 606/181 |
| 5,368,047 | A * | 11/1994 | Suzuki | A61B 5/150022 600/576 |
| 6,210,420 | B1 * | 4/2001 | Mauze | A61B 5/15186 606/181 |
| 6,332,871 | B1 * | 12/2001 | Douglas | A61B 5/14532 600/583 |
| 7,163,515 | B2 * | 1/2007 | McNenny | A61B 5/150213 600/573 |

(Continued)

*Primary Examiner* — Joshua E Freeman

(57) ABSTRACT

New projectiles specialized for creating and recovering trace evidence at a crime scene are provided. A wide variety of embodiments are provided, covering several use scenarios—including, but not limited to, home security devices, which may be built into an entryway or other building structure, and law enforcement guns. In some embodiments, a projectile within a projectile is provided, which fires in the direction of a primary impact. A sampler device is provided within some projectiles, which may comprise tracing barbs, containers for analytes and even a hypodermic extraction apparatus. In some embodiments, projectiles have rebounding devices, which may overlap with aspects of the sampler device, for developing distance from a criminal suspect. Other aspects, such as GPS, fasteners and defense mechanisms, are also disclosed, which encourage recovery by the authorized user and deter interception.

20 Claims, 10 Drawing Sheets

(56) References Cited

U.S. PATENT DOCUMENTS

| | | | | |
|---|---|---|---|---|
| 7,867,174 B2* | 1/2011 | Rivet | ............... | A61B 5/14 |
| | | | | 600/573 |
| 8,453,871 B2* | 6/2013 | Dunyon | ............... | B26F 1/14 |
| | | | | 220/745 |
| 8,464,451 B2* | 6/2013 | McRae | ............... | F41A 17/06 |
| | | | | 42/1.01 |
| 2002/0111565 A1* | 8/2002 | Roe | ............... | A61B 5/15186 |
| | | | | 600/578 |
| 2004/0133126 A1* | 7/2004 | McNenny | ............... | A61B 5/150213 |
| | | | | 600/573 |
| 2008/0010888 A1* | 1/2008 | Nerheim | ............... | F41H 13/0018 |
| | | | | 42/1.08 |
| 2008/0039962 A1* | 2/2008 | McRae | ............... | F41A 17/06 |
| | | | | 700/90 |
| 2009/0277065 A1* | 11/2009 | Clark | ............... | F41A 19/01 |
| | | | | 42/1.03 |
| 2015/0285601 A1* | 10/2015 | Knights | ............... | F42B 12/40 |
| | | | | 102/513 |
| 2015/0377572 A1* | 12/2015 | Darragjati | ............... | F41A 9/65 |
| | | | | 42/50 |
| 2016/0169603 A1* | 6/2016 | Stewart | ............... | F41A 17/06 |
| | | | | 42/1.01 |
| 2016/0377383 A1* | 12/2016 | Downing | ............... | F41G 3/165 |
| | | | | 42/111 |

* cited by examiner

PROJECTILES SPECIALIZED FOR DNA AND OTHER TRACE EVIDENCE COLLECTION

RELATED APPLICATION DATA

This application is a continuation-in-part of U.S. patent application Ser. No. 14/828,514, filed Aug. 17, 2015, now U.S. Pat. No. 9,423,223, which itself is a continuation-in-part of U.S. application Ser. No. 13/666,965, filed Nov. 2, 2012, now U.S. Pat. No. 9,109,864. The entire contents of each of those applications are hereby incorporated by reference into the present application as if fully set forth herein.

FIELD OF THE INVENTION

The present invention relates to the fields of weapons, aeronautics and police equipment. More specifically, the invention relates to missiles with actuators and deployment systems.

BACKGROUND

In modern warfare, missiles and bombs often implement explosive payloads detonated upon impact at a target, or at a related time and/or place. These payloads often involve combustion, and, therefore, the use of an oxidizer.

Certain missile and bomb systems, such as "fuel-air" and other thermobaric systems, spread explosive material into the atmosphere surrounding or within a target, to strengthen and/or extend an explosive impact. Typically, these systems use primary and secondary charges, where the primary charge serves to inject and/or spread explosive material into ambient air at the target, after which the secondary charge ignites the resulting mixture. Thermobaric bombs may amplify and extend the impact of an explosive payload generally, and may aid in overcoming obstacles, such as bunkers or other enemy cover.

Some missiles, such as ramjet missiles, involve air intake to aid in powering flight. Such missiles may operate at high speeds, including supersonic speeds, and may implement variable-inlet chins. See, e.g., U.S. Pat. No. 5,167,249. In these applications, the size of an air inlets may be varied to optimize air shock, efficiency and flight power.

Some projectiles predate humanity by millions of years, arising by evolution in the animal kingdom. For example, the Archerfish fires droplets of water at small insects, arachnids and lizards from a range of up to three meters, capturing them from plants overhanging its habitat. Archerfish evolved in the Eocene epoch, about 50 million years ago—long before humans existed, let alone developed projectile firing mechanisms. Some New World Tarantulas fire hairs from their abdomen as a defense mechanism. Even plants, like the Orange Jewelweed, Peet Mosses and Scotch Broom have evolved projectile firing mechanisms, to spread seeds.

Trace evidence is any residual material from the contact or presence of a person or object at a crime. Most if not all contacts between two materials will leave some trace evidence. Modern law enforcement may develop trace evidence by shaking, batting or scraping clothing worn by a victim, or other materials left about a crime scene, collecting the dirt, dander, blood, lint that falls off, and then analyzing it in a laboratory. DNA can sometimes be recovered and analyzed from trace evidence, using an amplifier, such as PCR, to reproduce much larger amounts of the genetic material. Simpler trace evidence, such as a victim's skull with blunt force trauma, has probably been used in some form by primitive law enforcement since the dawn of civilization.

SUMMARY OF THE INVENTION

New forms of projectiles configured to create and recover trace evidence from a crime scene are provided. A wide variety of embodiments are provided, covering several use scenarios—including, but not limited to, home security devices, which may be built into an entryway or other building structure, and law enforcement guns. In some embodiments, a projectile within a projectile is provided, which fires in the direction of a primary impact. A sampler device is provided within some projectiles, which may comprise tracing barbs, containers for analytes and even a hypodermic extraction apparatus. In some embodiments, projectiles have rebounding devices, which may overlap with aspects of the sampler device, for developing distance from a criminal suspect. Other aspects, such as GPS, fasteners and defense mechanisms, are also disclosed, which encourage recovery by the authorized user and deter interception.

A new form of missile, for implantation of an actuator within a wall or building, is provided. In some aspects of the invention, the missile comprises an enclosed actuator, deployed upon successful implantation of the missile in a target wall. Preferably, the missile comprises stops and piercing grips to secure the missile within the target wall, and encourage the proper degree of penetration and a mounting position enabling the deployment of the actuator(s) comprised within the missile. In some embodiments, the actuator can be remotely actuated by control system and user commands. The missile may be accelerated by an electromagnetic rail gun to a velocity, and comprised of ferromagnetic material(s) with a weight, encouraging the proper degree of implantation within the target wall. In some embodiments, the proper degree of implantation comprises passing a penetrating tip of the missile through an inner wall of a room, and clearing and opening hinged leaves to deploy the actuator within a room. In some aspects, the penetrating tip comprises sharp leading blades or edges for easing entry and implantation. Exemplary actuators include a firearm, camera, and nonlethal payload-releasing device. If remotely actuated, the missile preferably comprises communications hardware, and a local control unit, in communication with a larger missile control system, which may be managed by a user.

New missile systems are also provided, implementing reduced pre-deployment weight, higher impact and greater deployment flexibility, among other advantages. In some embodiments, mid-flight oxygen filtration from atmospheric air, followed by concentration, compression and/or storage in ideal oxidizer deployment locations, leads to enriched, greatly increased oxidizer load and/or greatly increased missile weight just prior to impact. Among many other benefits, missiles implementing aspects of the invention:

1.) Are far less volatile, and therefore safer, prior to deployment;
2.) May be flexibly-deployed as a (a) conventional explosive warhead, (b) a thermobaric warhead, (c) a mixture of the two, (d) an increased-weight kinetic weapon or (c) one of several yield sizes, coverages or burn rates, among other options, and such deployment options may be selected in-flight, for example, by tactical command;
3.) May be far lighter during transportation and platform maneuvers than conventional missiles with comparable warhead fuel; and 4.) The concentration of oxidizer may be more concentrated than with ambient oxygen, overcoming those limitations of current fuel/air and other thermobaric explosives.

These and other advantages of the present invention may be better understood by reviewing the more detailed aspect disclosures set forth below. It should be noted that the particular embodiments and terms set forth below are exemplary only, and that the scope of the invention includes any of virtually limitless other alternatives that may be substituted to carry out any aspect set forth below. As a rule of construction: where this application recites a number, gender or other specific qualifiers in the form of articles and pronouns, it should be understood that, where logically possible, any other number, gender or qualifier should also be separately read in as another alternative meaning or expression of the application.

DETAILED DESCRIPTION OF THE INVENTION

Figure 1:
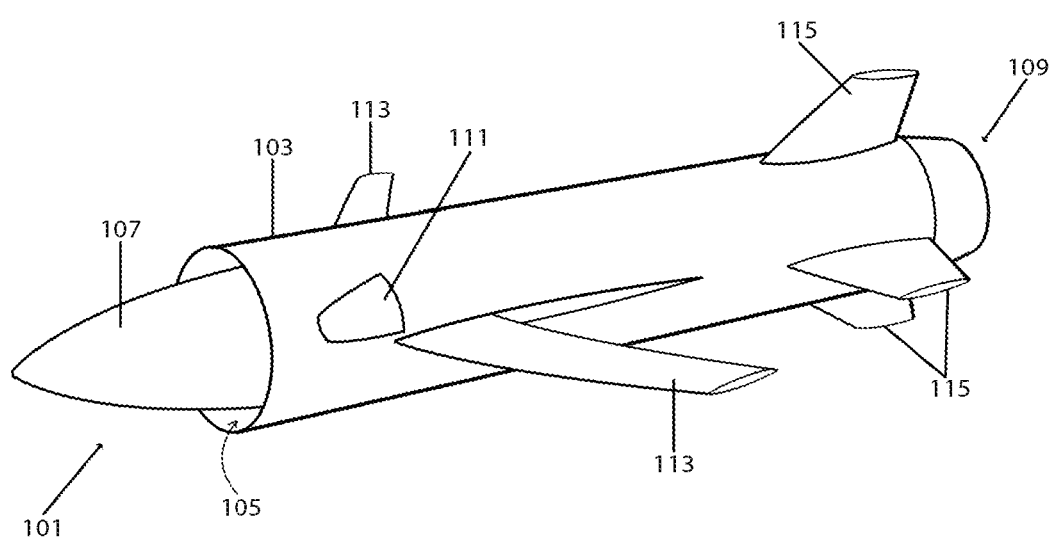
FIG. 1 is a perspective view of outer surfaces of an exemplary missile system that may be used to carry out aspects of the present invention.

FIG. 1 is a perspective view of outer surfaces of an exemplary missile system 101, which may be used to carry out aspects of the present invention. System 101 includes a missile housing 103, preferably with variable geometry and variable airflow aspects. For example, a variable-size air inlet 105 is partially variably-defined by an actuable nose piece 107. If selected by a user and/or control system, such as the system set forth in FIG. 5, nose piece 107 may retract inward and toward the tail end and thruster 109 of the missile, and thereby increase the size of the gap of the air inlet 105. When open, and in flight, the air inlet 105 may allow ambient air to flow inside the housing 103 and, as will be discussed in greater detail below, into various additional interior aspects for processing and storage functions. Such interior aspects may include intake(s) for jet propulsion (though they also may not, for example, if solid fuel rocket power is used) and power conversion but will, preferably at the user and/or system's election, include intakes for gas filtration and/or compression and/or storage. An airflow outlet may also be required to communicate with and/or service such interior aspects, and an exemplary pressure-reducing outlet panel louver 111 is pictured, which may draft for and reduce the outside air pressure onto, such an outlet—in part, to aid filtration aspects, as will be discussed in greater detail below. In addition, by varying airflow through such outlets at locations beneath and above wing and other aeronautically significant elements, and depending on the outlet airflow angles chosen (which may be variable by the system and/or user) the missile system may also aid in controlling lift, yaw, pitch, roll and other flight dynamics, as a side-benefit.

In addition to the variable-intake geometry discussed above, which may be variably actuated by, for example, servo motors controlled by the control system, the missile may include any conventional or known missile aspects, such as variable geometry wings 113, radial guidance and stabilization fins 115, and any other known missile embodiments and alternatives in the art. As explained elsewhere in this application, the exact designs depicted in this and other figures are exemplary only.

Figure 2:
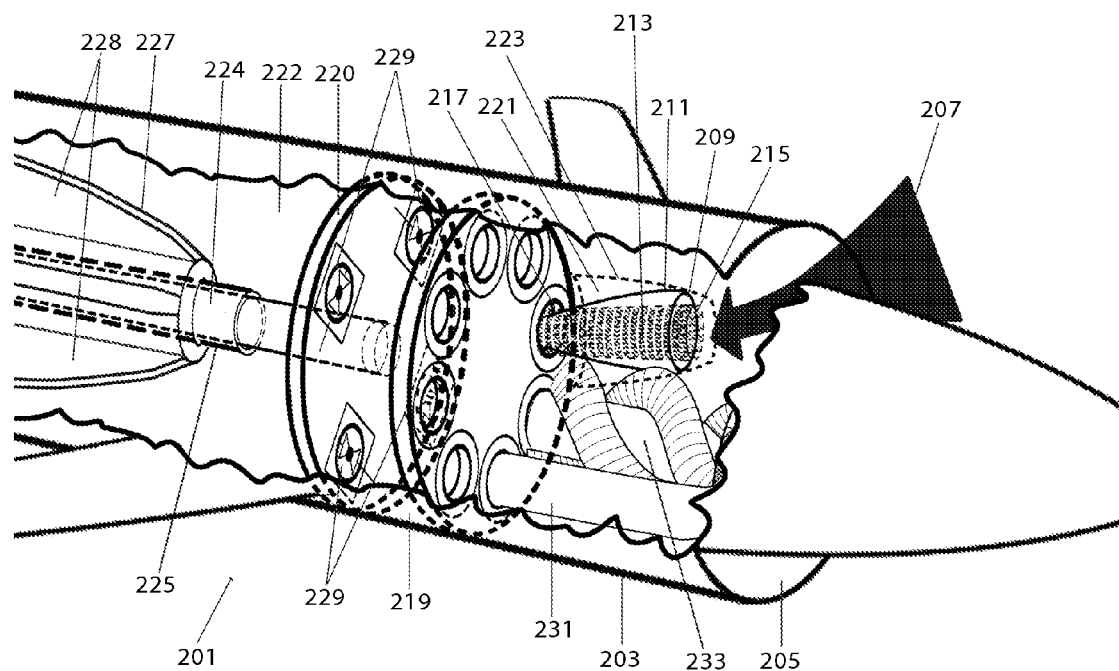
FIG. 2 is a partial view, in perspective and partly in section and schematic, showing some interior aspects an exemplary missile system that may be used to carry out aspects of the present invention.

FIG. 2 is a partial view, in perspective and partly in section and schematic, showing some interior aspects an exemplary missile system 201 that may be used to carry out aspects of the present invention. A missile housing 203 with a variable-size air inlet 205 leads in-flowing ambient air from the front of the missile due to flight (as shown by airflow representing arrow 207) to an inlet port 209 for an interior filter 211. Interior air filter 211 includes at least a portion of a filtration medium or element 213, for example a zeolite cylindrical matrix that preferentially absorbs nitrogen, as pictured, suitable for selectively absorbing and/or filtering ambient gases from the airflow 207 that then flows against and through it. Preferably, filtration element 213 may rotate or be actuated to rotate on an axis 215, such that a variable part of it may be exposed to airflow 207. As air flows over the exposed portion of element 213, nitrogen and other gases may be absorbed, and filtered out of the airflow, while oxygen-enriched air continues to flow toward the tail end of the filter 211, through a port 217 to an interior enriched gas intermediate storage chamber 219. Preferably, port 217 includes a one-way valve, permitting compresses and enriched airflow 207 (after it passes through filter element 213) into intermediate chamber 219, but not back into filter 211 from intermediate chamber 219.

Inlet 205 preferably comprises a relatively broad leading surface area engaging airflow 207 upon entry, and serves to funnel that airflow to a narrower surface area at the point of entry at the inlet port 209 of filter 211. As a result, upon entering filter 211, airflow 207 becomes more highly pressurized than it was prior to entering the missile housing 203. As filtration element 213 experiences pressurized airflow and selectively absorbs non-oxidizing gasses (including, but not limited to, nitrogen) in its portion exposed to that airflow, it may automatically, or by actuation by the system, rotate and thereby move a more saturated portion away from airflow 207, until that more saturated portion no longer is exposed to airflow 207 and instead faces and is housed within a pressure-reducing waste gas outlet volume 221, defined by a pressure-reducing exterior louver 223 (which may be similar to the louver 111 pictured from an exterior viewing angle in FIG. 1). Because the volume then housing the saturated portion of the filter element has greatly reduced gas pressure, gasses saturating that section, including nitrogen, then escape the filter element 213, rendering it desaturated again and ready for return to the pressurized (left-hand) section of the filter with the capacity to absorb more of such gasses from airflow 207. By virtue of the same rotation, a more desaturated portion of element 213 therefore becomes exposed to airflow 207, and more effectively selectively filters gases from it, further enriching airflow 207 with oxygen, which is selectively less absorbed. This rotation can be gradual, continuous or by degrees, even if driven or partially driven by the airflow itself—for example, due to spin-inducing surfaces on element 213 or an attached object—to optimize the effectiveness and efficiency of the filter. For example, sensors may indicate the concentration of oxygen and other atmospheric gases in the airflow upon exiting the filter in comparison to the concentration upon entrance to enable a control system to determine that effectiveness and efficiency, and, thereby, whether to rotate filter element 213. Alternatively, sensors may drive circulation or rotation of filtration element(s) in reaction to their saturation with filtered gases or in reaction to the concentration of waste gasses in volume 221. While this method of filtration and oxygen enrichment of airflow is preferred, it should be noted that any known method for filtering, concentrating and retaining oxidizing gasses, such as oxygen, from a gas mixture, such as atmospheric air, may, alternatively, be used and are within the scope of the invention. Some aspects of the invention (not pictured) may include auxiliary pressurizing devices for increasing the efficiency of filtration, as well as multiple filter tiers for removing additional non-oxidizing gasses.

After the airflow process described above, intermediate storage chamber 219 then contains oxygen-enriched air, which may be compressed by piston-compressor wall 220, and selectively passed to warhead/end storage unit volume 222. Compressor wall 220 may be driven by a piston-driving rod 224 within a rod guide 225. Rod guide 225 may also serve as a platform for shaped fuel and/or explosive charges and/or sections, such as that shown as 227, which include concavities 228 that encourage the mixture and dispersion of fuel with the concentrated oxidizing agents in unit 222 upon deployment of the warhead (which may be thought of as, at least, including unit 222) by detonator(s) (not pictured). Any known techniques for explosive ordinance and warhead deployment and detonation may be used in conjunction with the aspects of the invention herein discussed, and such techniques should be understood to be included in the scope of the invention as if set forth in detail here.

Control valves, such as those pictured as 229, which may be controlled by the control system or locally controlled by pressure, concentration, volatility and/or other sensors, may permit compressed and enriched oxidizing gas to pass from intermediate chamber 219 into warhead/end storage unit volume 222 when sufficient (and/or not too great) compression, oxygen enrichment and other factors indicating desirable gas conditions for storage are sensed. Such sensors may be on or about wall 220 and/or intermediate chamber 219 and warhead/end storage unit volume 222, and the standards for assessing adequate conditions may be altered according to mission parameters, desired detonation strength or detonation nature (or lack thereof, if a purely kinetic weapon is selected) and such parameters may be variably set, even mid-mission, by the control system—which may be in communication with and include distant, real-time tactical command elements. Assuming that a large-yield oxidizing agent-enriched detonation(s) is/are required at or about a target, however, and further assuming that the concentration of enriched oxygen within intermediate chamber 219 is determined to be insufficient by the control system, the control system may not yet actuate compression and transfer to warhead/end storage unit 222 by compression wall 221 and its control valves 229. Instead, the system may drive or permit further enrichment of the same gas by the same or (as pictured) additional filtration elements. Those additional filtration elements may include a circulation pump and recirculation channeling, which may be external to intermediate chamber 219 to enable full use of 219's volume by compression elements, such as wall 220. More specifically, a recirculation outlet tube 231 may conduct gas from intermediate chamber 219 into the front of a turbine-driven filtration element 233, which may further enrich the gas and pass it once again to intermediate chamber 219. Such a refiltration circuit comprising 231 and 233 may be selectively driven by the control system in such amounts and for such time as may be required for the mission. These refiltration elements will be discussed in greater detail in reference to FIG. 3.

As discussed elsewhere in this application, various warhead mode selections may be made by a Command and Control for execution by the system, including modes that change the deployment, concentration and compression of fuel and oxidizer. In addition, the timing of detonation aspects may be dictated by such modes, including dictating primary (scattering) and secondary or tertiary (post obstacle ignition) charges for maximizing impact within closed or guarded targets, such as bunkers. In addition to other such modes, pressure sensors may be used (which may include some sensors discussed above, that survive an initial housing breach or are otherwise exposed to a penetrated target environment) that sense the pressure differential upon penetrating a more confined space from a more open atmosphere, and trigger detonation after such time to penetrate protective walls and other obstacles prior to deployment of ordinance. A split-function deployment may also be used, for example, in which gun firing elements to clear outer-bunker regions, or sound or electromagnetic-disruption elements targeting enemy personnel and materiel, to prevent reaction to the missile, may also be directed in a mode and implemented, if available within the missile system. Any other known warhead or missile ordinance deployment methods or modes may also, or alternatively, be used.

Figure 3:
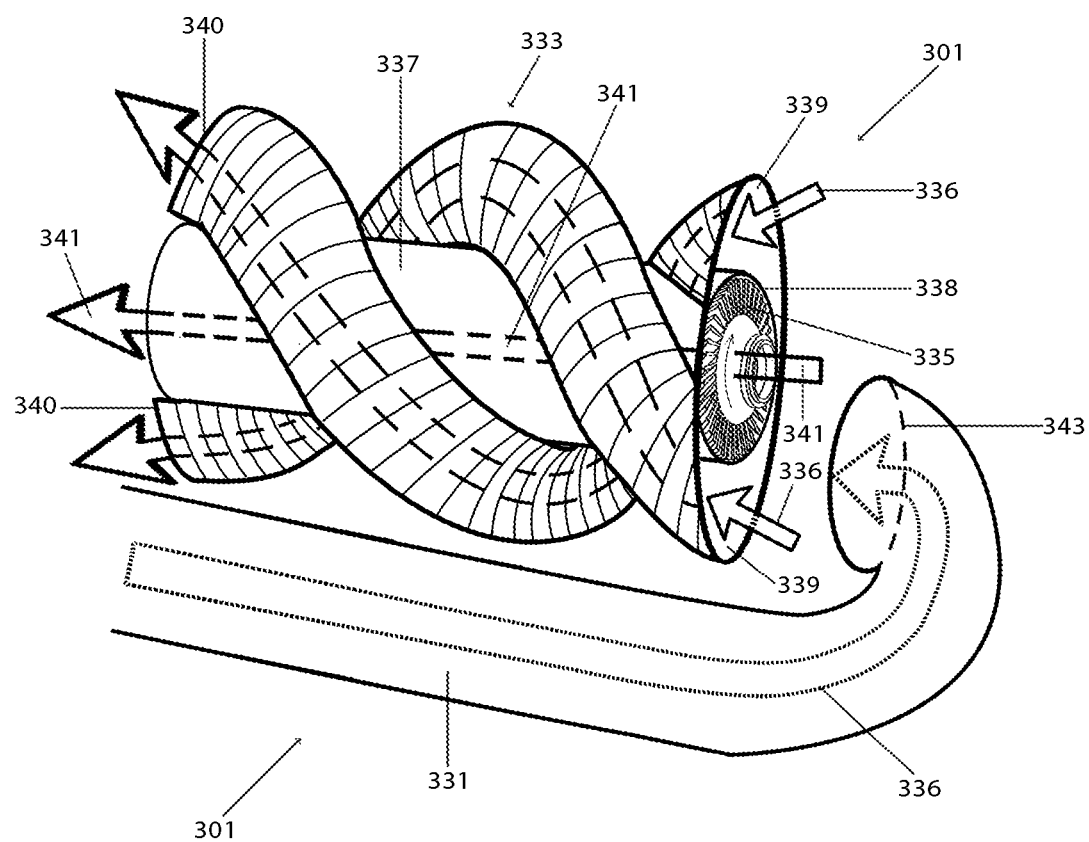
FIG. 3 is a larger, more detailed perspective view of exemplary oxidizer concentration elements discussed previously in FIG. 2.

FIG. 3 is a larger, more detailed perspective view of the exemplary oxidizing agent concentration elements 301, discussed immediately above, in reference to FIG. 2. More specifically, a recirculation tube 331 (previously, 231) and a turbine-driven filtration element 333 (previously 233) are shown separated from one another and the remainder of the exemplary system set forth in FIG. 2. Filtration element 333 includes a central turbo/turbine 335 that may drive recirculation airflow (shown by airflow indicating arrow 336) into a central tube 337, which also at least partially contains the airflow-driving and driven turbine 335. To maximize efficiency, turbine 335 may be driven, at least in part, by an external airflow (depicted by airflow-indicating arrows 336) entering turbocharging tube inlets 339, and exiting both element 333 and the entire missile system through its side housing via outlets 340. Preferably, the turbine 335 is at least partially driven by that external airflow, but that external airflow does not mix with the internal gas airflow, shown by airflow arrow 341 (which is oxidizing agent-enriched) due to gas separation walls between the turbine and turbocharging airflow drivers (not pictured). Although shown separated to reveal detail, in operation, end 343 of tube 331 connects with and forms a complementary, airtight seal with port 338 of central tube 337 and, at its other end, is in communication with a gas storage chamber (for example, intermediate chamber 219 of FIG. 2).

Figure 4:
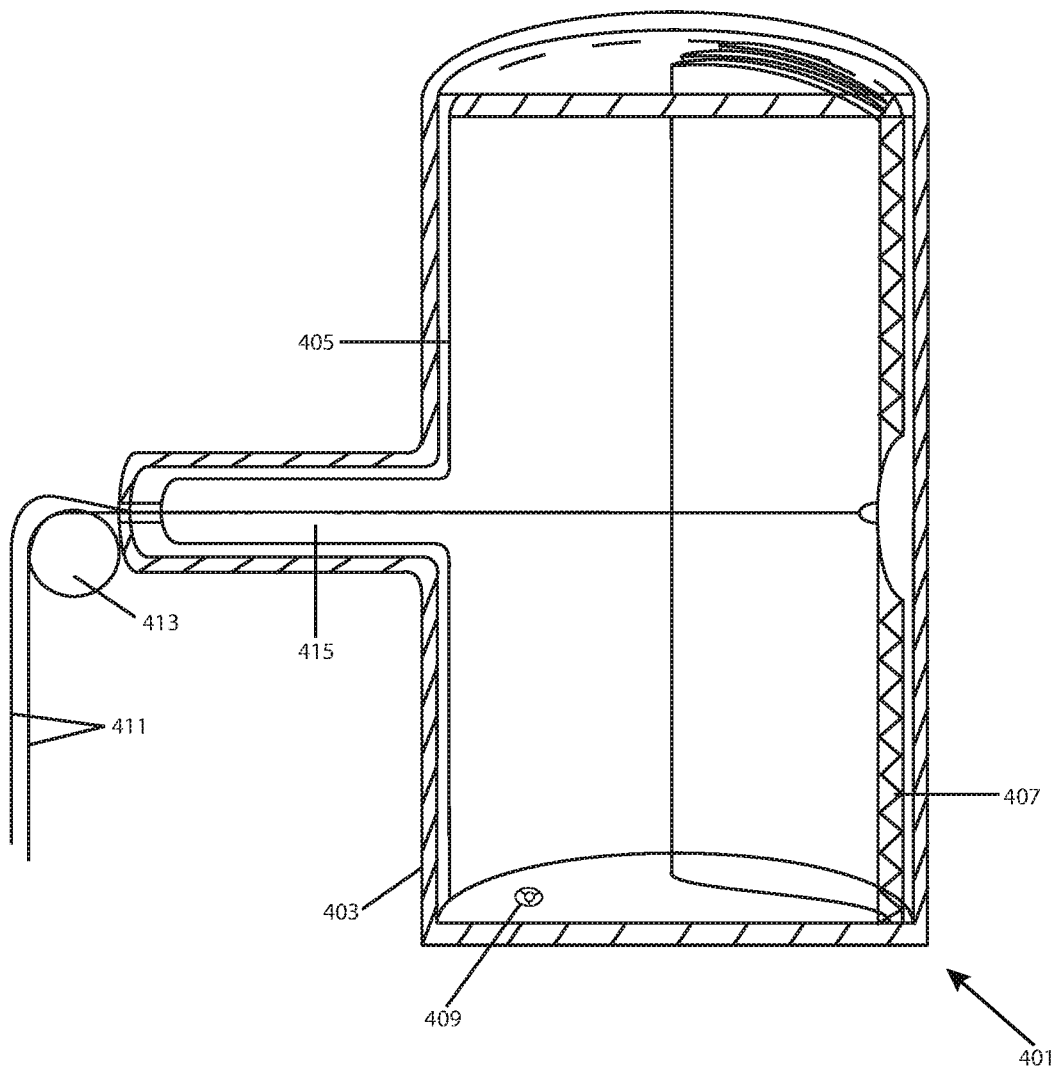
FIG. 4 depicts some alternative exemplary gas compression aspects, using structural potential energy, that may be used in conjunction with aspects of the present invention.

FIG. 4 is a cross-section view depicting alternative exemplary compression aspects 401, implementing structural potential energy, that may be used in conjunction with aspects of the present invention. In FIGS. 2 and 3, an exemplary reciprocating piston-type compression system was described to carry out certain aspects of the invention. It should be understood that a wide variety of other techniques for gas compression, some of which are known in the art, may also be used, alternatively or in conjunction with piston compression. For example, axial flow or centrifugal compression techniques may be used. FIG. 4 depicts a new form of compressor driven by mechanically-stored energy, to minimize weight costs, that may be more great in other energy storage and/or translation techniques used to drive or assist gas compression.

In general, the compression aspects shown in FIG. 4 may use a series of tensioned dynamic storage volume walls to both define and compress a series of variable compression sub-chambers. Prior to deployment, at least one outer layer 403 may, at least in part, define a compressed gas storage volume (which may be part of a warhead, as with unit/volume 222 from FIG. 2, and mounted within a larger missile or bomb structure and system). Unlike other, tensioned layers, which will be described below, outer layer 403 maintains a substantially fixed shape and is not tensioned or bistable, except that it may be to the degree necessary to maintain a pre-deployment vacuum. That shape is approximately cylindrical, and shown in central section along its vertical axis. However, a series of variably-positioned inner compartment-defining walls, such as those partially shown as 405 and 407, are variably tensioned and bistable. In their initial, pre-deployment configuration, any such layers may be in a structural position and configuration shown approximately by 407. Specifically, the walls 407 of a chamber are compacted to the right-hand-side of the storage volume (from the perspective of the viewer of the figure). In this compacted state, several of the vertical sections or members comprised in wall 407 are force loaded against the strength of the outer layer 403 or other structures, and have a high potential energy compared to an uncompacted state, approximately shown by the configuration of wall 405. Such an uncompacted state is the second bistable configuration of inner chamber defining walls, such as 405 and 407, and, thus, transition from the state shown as 407 to that shown as 405 involves a great release of structurally stored energy, which is used to compress gas within such inner chambers. A variable valve (or valves) such as that pictured as 409 permit the mid-missile-deployment-flight filling of the volume defined by outer layer 403, and/or sub-volumes defined by inner chamber walls such as 405 and 407. As such filling takes place (which may be aided by an initial vacuum in the volume defined by these walls), valve(s) 409 may close, or simply be one-way valves prohibiting gas emission from the chamber and sub-chambers, and trigger transition of inner layers (one-per complete volumetric filling) from the high energy bistable state (shown by 407) to the low-energy bistable state (shown by 405). In so transitioning, an inner-chamber defining layer (such as 405 or 407) greatly compresses gasses held in the volume and within those layers, creating a sub-chamber that is a fraction of the overall storage volume. These transitions and compressions may be accomplished or aided by internal air compression gates or valves, on inner chamber walls, such as 405 and 407. Such valves or gates, or valve(s) 409 then may seal such compressed inner layers and the outer layer, but 409 may reopen to permit gasses to fill the next inner layer, such as 407, then next available for filling, bistable transition, and further compression of the next filled remaining volume held within a bistable, sealable subchamber (preferably, sealed just prior to filling and bistable transition). Further structural energy loading may be included, for example, with a series of tensioned cables such as those partially depicted by 411 and/or external reel 413, to assist layers such as 405 and 407 in transitioning from one to the other bistable state, and for assisting in compression of confined air within each sub-chamber at the appropriate time(s) (as may be automatically triggered by partial transition, pressure changes and/or sensors, sensor/motors and a control system, such as, but not limited to, the control system discussed in reference to FIG. 5). If a great excess of wall length results, which cannot be fully held within the outer volume defined by 403, from transition to an uncompacted state, a relief section within outer layer 403, such as 415, for holding excess length of wall or other tensioning members, may also be used.

Figure 5:
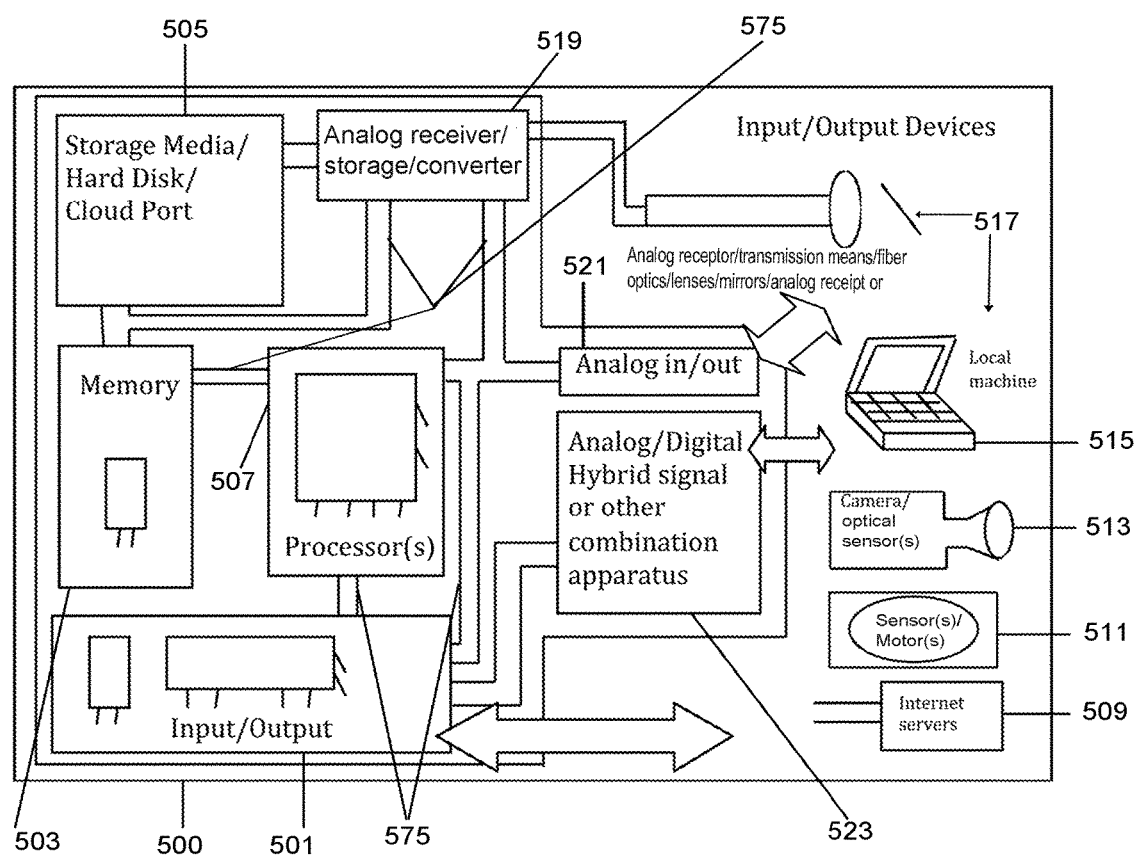
FIG. 5 is a schematic block diagram of some elements of an exemplary control system that may be used in accordance with aspects of the present invention.

FIG. 5 is a schematic block diagram of some elements of an exemplary system 500 that may be used in accordance with aspects of the present invention, such as, but not limited to, sensing gas and physical member compression and gas concentrations and actuating servo/motors and control valves, and receiving control commands and managing input interfaces from a Control and Command, as defined and discussed elsewhere in this application. The generic and other components and aspects described herein are not exhaustive of the many different systems and variations, including a number of possible hardware aspects and machine-readable media that might be used, in accordance with the present invention. Rather, the system 500 is described to make clear how aspects may be implemented. Among other components, the system 500 includes an input/output device 501, a memory device 503, storage media and/or hard disk recorder and/or cloud storage port or connection device 505, and a processor or processors 507. The processor(s) 507 is (are) capable of receiving, interpreting, processing and manipulating signals and executing instructions for further processing and for output, pre-output or storage in and outside of the system. The processor(s) 507 may be general or multipurpose, single- or multi-threaded, and may have a single core or several processor cores, including microprocessors. Among other things, the processor(s) 507 is/are capable of processing signals and instructions for the input/output device 501, analog receiver/storage/converter device 519, and/or analog in/out device 521, to cause a display, light-affecting apparatus and/or other user interface with active physical controls to be provided for use by a user on hardware, such as a personal computer monitor (including, but not limited to, monitors or touch-actuable displays) or terminal monitor with a mouse and keyboard or other input hardware and presentation and input software (as in a GUI), and/or other physical controls.

For example, and with particular emphasis on the aspects discussed below, in connection with FIGS. 9 through 12, the system may carry out any aspects of the present invention as necessary with associated hardware and using specialized software, including, but not limited to, window presentation user interface aspects that may present a user with a representation of a missile target(s) and present command and control options to, for example, eject projectiles and secondary projectiles, plant tags, select and move missile control commands (e.g., mouse with cursor or keyboard arrows or joystick or, for example, with dropdown menus, select among various warhead deployment orders) with different settings for each such command. As another example, with reference to FIGS. 1-4, such software may, with or without the presentation of options to a user for selection on a conventional display, carry out any control aspect of the invention as necessary, such as, but not limited to, sensing and implementing compression pressures and gas concentrations, controlling control valves depending on sensor measurements and timing, targeting, warhead conditioning and deployment, identifying a reference point for an observation point, determining a range of possible or likely observation points, and implementing other user interface and processing aspects that may be used in the art, such as physics engines, physical modeling, detection, image-creation and remote control (and related software).

The processor 507 is capable of processing instructions stored in memory devices 505 and/or 503 (or ROM or RAM), and may communicate via system buses 575. Input/output device 501 is capable of input/output operations for the system, and may include any number of input and/or output hardware, such as a computer mouse, keyboard, networked or connected second computer, camera(s) or scanner(s), sensor(s), sensor/motor(s), range-finders, GPS systems, other Command and Control centers, electromagnetic actuator(s), mixing board, reel-to-reel tape recorder, external hard disk recorder, additional hardware controls and actuators, directional shading matrices, directionally-actuable light sources with variable collimation and shiftable bases, additional movie and/or sound editing system or gear, speakers, external filter, amp, preamp, equalizer, computer display screen or touch screen. It is to be understood that the input and output of the system may be in any useable form, including, but not limited to, signals, data, and commands/instructions. Such a display device or unit and other input/output devices could implement a user interface created by machine-readable means, such as software, permitting the user to carry out the user settings, commands and input discussed in this application.

501, 503, 505, 507, 519, 521 and 523 are connected and able to communicate communications, transmissions and instructions via system busses 575. Storage media and/or hard disk recorder and/or cloud storage port or connection device 505 is capable of providing mass storage for the system, and may be a computer-readable medium, may be a connected mass storage device (e.g., flash drive or other drive connected to a U.S.B. port or Wi-Fi) may use back-end (with or without middle-ware) or cloud storage over a network (e.g., the internet) as either a memory backup for an internal mass storage device or as a primary memory storage means, or may simply be an internal mass storage device, such as a computer hard drive or optical drive.

Generally speaking, the system may be implemented as a client/server arrangement, where features of the invention are performed on a remote server, networked to the client and made a client and server by software on both the client computer and server computer. Input and output devices may deliver their input and receive output by any known means of communicating and/or transmitting communications, signals, commands and/or data input/output, including, but not limited to, the examples shown as 517, such as 509, 511, 513 and 515 and any other devices, hardware or other input/output generating and receiving aspects. Any phenomenon that may be sensed may be managed, manipulated and distributed and may be taken or converted as input or output through any sensor or carrier known in the art. In addition, directly carried elements (for example a light stream taken by fiber optics from a view of a scene) may be directly managed, manipulated and distributed in whole or in part to enhance output, and whole ambient light information for an environmental region may be taken by a series of sensors dedicated to angles of detection, or an omnidirectional sensor or series of sensors which record direction as well as the presence of photons recorded, and may exclude the need for lenses or point sensors (or ignore or re-purpose sensors "out of focal plane" for detecting bokeh information or enhancing resolution as focal lengths and apertures are selected), only later to be analyzed and rendered into focal planes or fields of a user's choice through the system. While this example is illustrative, it is understood that any form of electromagnetism, compression wave or other sensory phenomenon may include such sensory directional and 3D locational information, which may also be made possible by multiple locations of sensing, preferably, in a similar, if not identical, time frame. The system may condition, select all or part of, alter and/or generate composites from all or part of such direct or analog image transmissions, and may combine them with other forms of image data, such as digital image files, if such direct or data encoded sources are used.

While the illustrated system example 500 may be helpful to understand the implementation of aspects of the invention, it is understood that any form of computer system may be used to implement many aspects of the invention—for example, a simpler computer system containing just a processor (datapath and control) for executing instructions from a memory or transmission source. The aspects or features set forth may be implemented with, and in any combination of, digital electronic circuitry, hardware, software, firmware, or in analog or direct (such as light-based or analog electronic or magnetic or direct transmission, without translation and the attendant degradation, of the image medium) circuitry or associational storage and transmission, any of which may be aided with external detail or aspect enhancing media from external hardware and software, optionally, by networked connection, such as by LAN, WAN or the many connections forming the internet. The system can be embodied in a tangibly-stored computer program, as by a machine-readable medium and propagated signal, for execution by a programmable processor. The method steps of the embodiments of the present invention may be performed by such a programmable processor, executing a program of instructions, operating on input and output, and generating output. A computer program includes instructions for a computer to carry out a particular activity to bring about a particular result, and may be written in any programming language, including compiled and uncompiled, interpreted languages, assembly languages and machine language, and can be deployed in any form, including a complete program, module, component, subroutine, or other suitable routine for a computer program.

Figure 6:
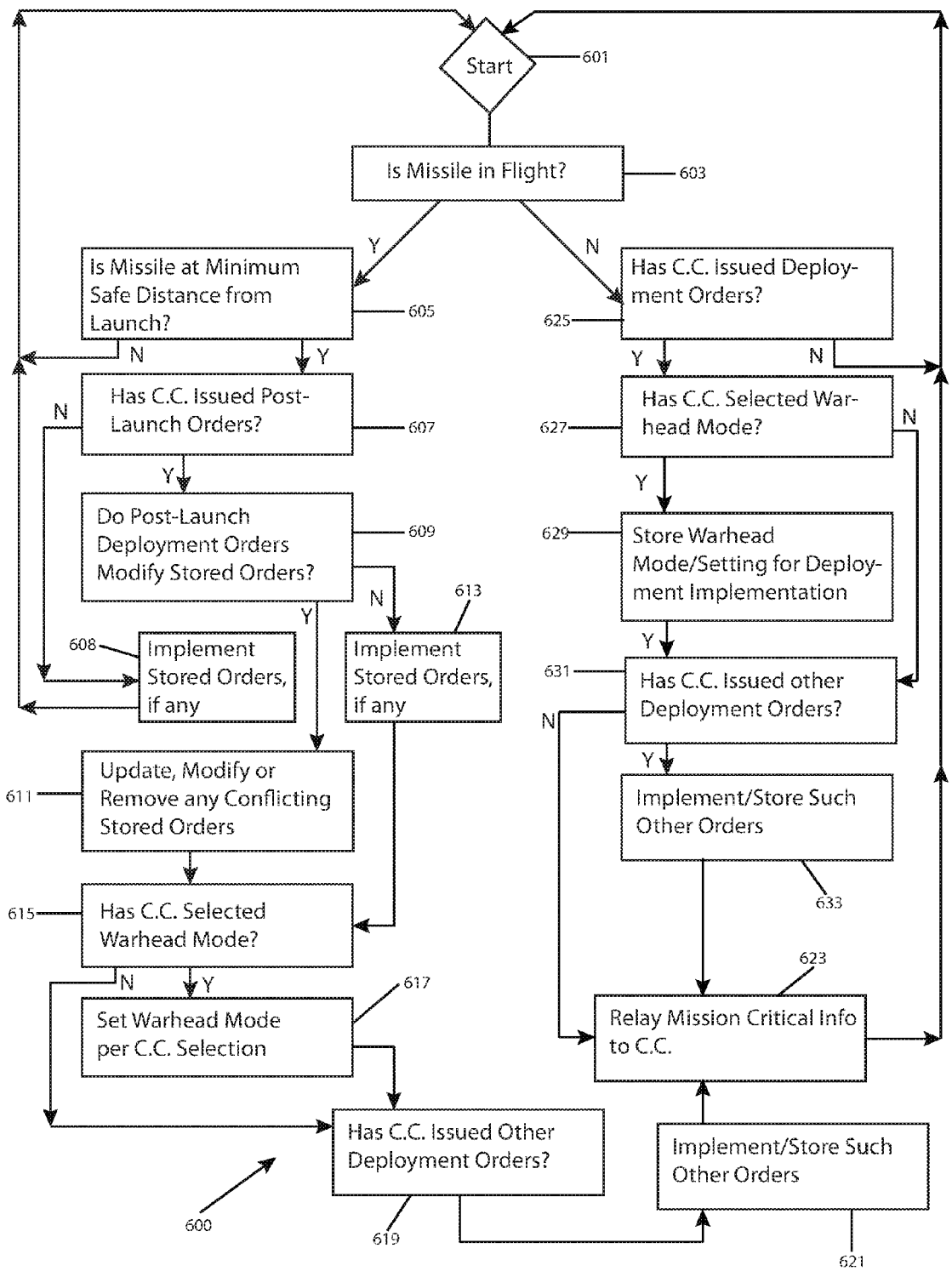
FIG. 6 is a process flow diagram of exemplary steps that may be taken by a system, such as a hardware and software system, implementing aspects of the present invention.

FIG. 6 is a process flow diagram of exemplary steps 600 that may be taken by a system, for example, a hardware and software control system, such as the system discussed above with reference to FIG. 5, implementing certain user interface and missile control aspects of the present invention. Although the process described with reference to FIG. 6 is preferred, and serves to illustrate aspects of the invention, it should be understood that a wide variety of alternative processes may implement aspects of the present invention, and are within its scope. In step 601, the process begins and proceeds to step 603, in which the system determines if an outbound missile subject to control by the system is in flight. Although not shown in FIG. 6, it should be understood that such determinations ordinarily will be made by a remote, secure communication system and transmitted between an on-board missile receiving system and a remote command and control center ("Command and Control" or "C.C.") which originates and implements commands, orders, instructions, selections and decisions from a user and/or systematic decisionmaker(s). If such a missile subject to the system's control is detected to be in flight, for example, by flight-indicating tracking systems and/or sensors, the system proceeds to step 605. If not, however, the system proceeds to step 625, and various pre-launch system steps, which will be discussed in more detail below.

In step 605, the system may determine whether the missile is currently located at a minimum safe distance for warhead armament and mode initiation, which minimum safe distance may be variably set based on the type of missile, missile altitude, speed, other environmental factors, the warhead, and possible warhead modes, and based upon other user and/or system settings, which may be variable. The minimum safe distance may be measured from the launch site and/or other areas to be protected from accidental weapon detonation. If the missile has not reached at least a minimum safe distance with respect to at least one such protected area, the system may implement or retain safety controls in the missile to maintain disarmament of the warhead and prevent the initiation of other warhead modes, and the system returns to the starting position.

If the missile has reached at least a minimum safe distance with respect to each such protected area, however, the system proceeds to step 607, in which it determines whether Command and Control has issued post-launch orders relevant to the missile's deployment. If not, the system next determines whether previously-stored orders (for example, from commands given prior to missile flight) have been recorded and, if so, implements them in step 608, and, in any event, the system then returns to the starting position. If the system instead determines at step 607 that post-launch orders have been issued, the system instead proceeds to step 609, in which it determines whether such current, post-launch orders modify or otherwise conflict with any prior stored orders. If so, the system proceeds to step 611, in which it resolves any such conflict in favor of the more current orders by updating, modifying and/or removing the conflicting prior stored orders, such that they no longer conflict. If no such conflict is found, however, the system instead proceeds to step 613 and implements the prior orders. In either event, the system next proceeds to step 615, in which it determines whether, among the post-launch commands, Command and Control has ordered selection of a Warhead Mode. As mentioned above, a warhead according to aspects of the present invention may be user variable, and "dialed in" for particular tactical objectives, even post-launch and in mid-flight, for example, if the missile is ordered to loiter while Command and Control determines what action to take with respect to a target. For example, as discussed above, in one setting, the warhead may begin to be charged with a maximum concentration and compression of mid-flight loaded oxidizer, and charges may be optimally engaged and/or positioned by servo/motors, thereby implementing a maximum yield warhead. As another warhead setting alternative, near the other side of the yield spectrum, a low concentration of oxidizer or non-oxidizer may be loaded to maximize momentum for a kinetic deployment only, and no explosion. In addition, infinite settings between or about these extremes may be selected. Whatever the selected setting, the system implements such Warhead Mode settings in step 617, and then proceeds to steps 619 and 621, in which it implements or stores additional orders, as necessary, from Command and Control, if any. If, in step 615, no Warhead Mode settings have been entered by Command and Control, the system proceeds directly to steps 619 and 621, skipping step 617. In either case, after step 621, the system proceeds to step 623, in which it may receive important mission-relevant information from any source, such as from on-board tracking and sensors aboard the missile, or other sources, and relays representations of such information to Command and Control. After step 623, the system returns to the starting position.

Returning to the starting position, and first step 603, if the system determines that the missile is not yet in flight, Command and Control may nonetheless proceed to several useful pre-launch system steps, beginning with step 625. In step 625, the system determines whether Command and Control has issued any orders related to missile deployment. If not, the system returns to the starting position. If so, however, the system next proceeds to step 627, in which it may determine whether Command and Control has selected a Warhead Mode, such as those discussed above with respect to step 615. If so, the system stores that selection in step 629 as an order for implementation after launch (after minimum safe distance, and if not overridden by conflicting in-flight orders, as discussed above). After step 629, or directly after step 627 if no Warhead Mode selection was made, the system next proceeds to step 631, in which it determines whether Command and Control has issued any other relevant orders for the system and, if so, proceeds to implement or store such orders in step 633. In any event, before returning to the starting position, the system may again relay any mission critical information to command and control, in step 623.

Figure 7:
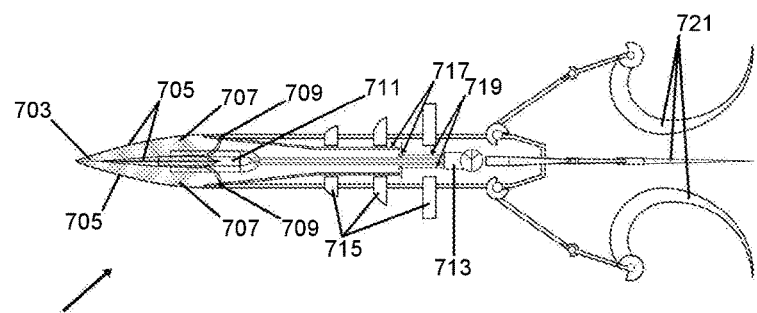
FIG. 7 is a side view of an exemplary ballistic missile configured to penetrate through and mount an actuable device into a target interior wall, in accordance with aspects of the present invention.

FIG. 7 is a side view of a specialized ballistic missile 701 configured to penetrate through and mount an actuable device into a target interior wall, in accordance with aspects of the present invention. A bladed leading tip 703 appears on the left-hand side of the figure, and comprises four sharpened blade edges 705 (three visible in the perspective of the figure) that facilitate missile 701's penetration of and proper mounting in a target wall. The number of blade edges 705 pictured is exemplary, and other arrangements, shapes, sizes and numbers of blade edges may alternatively, or in addition, be used while carrying out aspects of the present invention. Furthermore, in some aspects and embodiments, facilitating blades 705 may be omitted. In any event, leading tip 703 is preferably pointed, also to aid in penetration and mounting of missile 701 in a wall.

In some embodiments, tip 703 is comprised of at least one (and preferably a plurality) of hinged leaves 707. When leading tip 703 pierces and penetrates a target wall (e.g., when launched leftward, in the perspective of the figure, into a wall), the resulting inward pressure from the wall against tip 703 causes each of leaves 707 to be pressed together, creating reactive, normal forces against the wall, aiding in piercing it—preferably, with the aid of wall-slicing blade edges 705.

Figure 8:
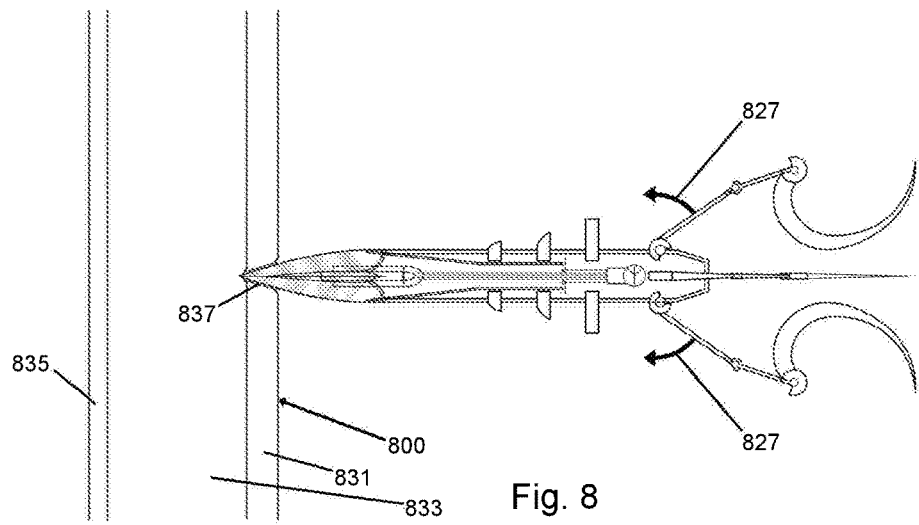
FIG. 8 is a side view of the same ballistic missile as discussed in reference to FIG. 7, above, in the process of piercing and being implanted in a target wall of a building.

As missile 701 penetrates more deeply into a target wall, however, such as wall 801 of FIG. 8, it eventually emerges, clear of those inward, compressive forces. In that instance, rotational force springs within leaf hinges 709 cause each of leaves 707 to open, as pictured in FIG. 8a, and expose and activate an internally-stored actuator device 711.

To prevent the opening of leaves 707 until proper, complete penetration or mounting of missile 701 (as will be demonstrated with reference to FIG. 8a, below, penetration depth sensors or wall clearance sensors or devices may be used, such as missile-arresting blocks 712. As will be discussed in greater detail below, in reference to FIG. 8a, missile-arresting blocks, such as the examples shown as 715, trigger internal contacts (such as examples 717) together when missile 701 penetrates a target wall. Contacts 717 are touch sensitive and release or drive leaves 707 open (for example by completing a circuit with blocks 712 when they are driven inward toward contacts 717 by inward pressures from the target wall as it is penetrated). In some embodiments, at least one of contacts 717 may also be a physical lever, pivoting on hinges 709, and physically trigger the opening of leaves 707 by pushing them open. In embodiments utilizing electronic contacts, a control unit 713, such as the control unit discussed in reference to FIG. 5, may be attached to, communicate with and control such sensors, and control rotational actuators driving hinges 709—for example, via internal wiring 719. In other embodiments, a combination of acceleration- and collision-driven mechanical catches and springs may be used to carry out the exposure and activation of the internally-stored actuator device 711, as will be discussed further below.

Collision-activated wall-sinking and grasping claws 721, which also serve as flight-stabilizing fins when in the in-flight configuration pictured in FIG. 8, are also included in missile 701. Preferably, three or four of such fins/claws 721 are included (a configuration with four being shown in FIG. 8). Claws 721 are driven by motorized hinges, which may be activated and powered by control unit 713, to rotate and pierce a target wall, gripping it. Thus, when missile 701 penetrates and properly mounts into a target wall, as shown in FIG. 8a, blocks 712 signal control unit 713 due to reactionary forces from the penetrated wall, and trigger the control unit to power hinges 723 to unlock arms 725 from the position pictured in FIG. 8 and rotate claws 721 into the target wall, as also shown in FIG. 8a. The deceleration forces from the impact of missile 701, and especially of the blocks 715 (and even more especially, of the final, rear-most block 715 (right-most in the figure) may also aid in unlocking and rotating hinges 723 and arms 725, and encourage their deep seating into the target wall upon collision. Stops 727 prevent over-rotation of hinges 723, maintaining their operational range between the in-flight position (shown in FIGS. 7 and 8) and their wall-piercing and gripping position (shown in FIG. 8a). In some embodiments, the control unit may not electrically power and control the rotation of the hinges 723 and, instead, rotational springs and catches may fully control and power the rotational movement of hinges 723, arms 725. In those embodiments, physical stops or catches prevent the administration of rotational force from springs driving movement of claws 721 into the target wall until substantial deceleration of the missile 701 from collision with a target wall. After rotation due to collision, however, which overcomes those stops or catches (or, in a preferred embodiment, reverses the spring force by pulling the spring onto an opposing side of arms 725) the springs driving the rotation of hinges 723 and arms 725 cause their forceful rotation into the position shown in FIG. 8a (as shown by initial motion/acceleration arrows 827).

FIG. 8 is a side view of the same ballistic missile 701 as discussed in reference to FIG. 7, above, in the process of piercing and being implanted in a target wall 800 of a building. Exemplary target wall 800 comprises an outer wooden board 831, an insulation section 833, and a drywall board 835. In the exemplary perspective of the figure, leading tip 703 has pierced outer board 831, creating a widening entry hole 837. As discussed above, as hole 837 widens during entry of missile 701, resulting inward pressure on the outer surfaces of leaves 707 maintains their closure during the impact. As missile 701 encounters physical resistance from penetrating wall 800, it begins to decelerate. That deceleration increases as blocks 715 next encounter the target wall, as missile 701 travels deeper (from right-to-left, in the perspective of the figure). In this process, the first, left-most of blocks 715 will be first to collide with outer board 831, followed by the central block. Each of these two, initial-entry blocks have sloped outer surfaces, to permit them to continue passing into wall 800. However, the final, rear-most block of blocks 715 does not comprise such penetration-easing sloped surfaces. Thus, in FIG. 8a, missile 701 comes to a rest with the rear-most blocks set flat against outer board 831.

Although a typical wall construction is pictured for target wall 800, it should be understood that missile 701 may take on different lengths, shapes, weights, materials and other configurations optimized for walls of varying thicknesses and material compositions. The exact missile design and target wall shown are exemplary only.

Figure 8A:
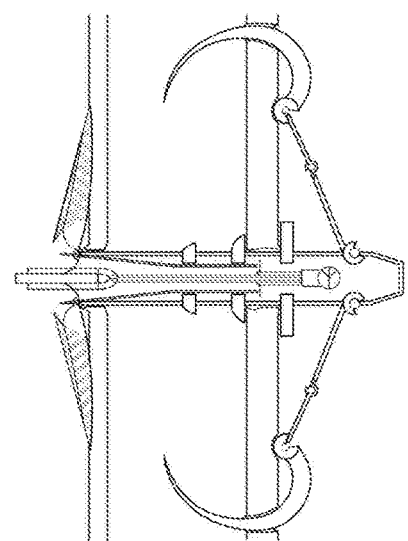
FIG. 8a is a side view of the same missile and target wall of FIG. 8, at a later time than that pictured in FIG. 8, when an actuator within the missile has been deployed.

FIG. 8a is a side view of the same missile and target wall of FIG. 8, at a later time than that pictured in FIG. 8, when tip 703 has passed through the inner side of target wall 800, and hinged leaves 707 have opened to deploy inner actuator 711. In practice, the point in time pictured may be under several milliseconds after the time period shown in FIG. 8, above and, even more preferably, under 30 milliseconds. As discussed above, the leading sets of blocks 715 have passed into wall 800 and, by resulting being pressed inward, have triggered the opening of leaves 707, which are now shown flayed outward, against the inner surface of wall 800 (exposed to the interior of a target room of building).

At this stage, after exposing actuator 711 to the interior of the room or building (for example, after a user targets and launches missile 701 into the position pictured in FIG. 8a) actuator 711 may be automatically, instantly activated or triggered, depending on mission objectives and the nature of the actuator 711. In other embodiments, however, a user may have remote control over the activation and operation of actuator 711, and may monitor activity within the room or building using actuator 711 (for example, if actuator 711 comprises a remote-feed camera, microphone or other sensor(s)) to determine next actions. Actuator types may include any form of actuator known in the art for tactical deployment, including, but not limited to: a firearm, a non-lethal weapon or personnel-stunning or disabling device (e.g., sedating gas, electromagnetic stun gun, rubber projectile launcher), or monitoring device (e.g., a camera). Remote control over missile 701 may be accomplished as discussed above via on-board control unit 713, via wireless communications antenna 714. For example, a user may operate a remote terminal and control unit, such as the control unit discussed above with reference to FIG. 5, also with its own wireless communications antenna, to issue command and control orders governing the operation of missile 701 and its comprised actuator 711. In some embodiments, the operation of actuator 711 may aided by live data and feedback gathered by actuator 711 or missile 701, and a control unit may autonomously order instantaneous reactions to those data, or a user may do so. For example, in one embodiment, upon mounting and activation of actuator 711, a camera and directional microphone may monitor the room breached for movements and, if movements are detected, aim at and deploy a payload toward the movement—for example, through the use of aiming actuators also in communication with control unit 713 and/or a control unit governing control unit 713, such as the remote terminal control unit, discussed above.

As can be seen in FIG. 8*a*, claws 721 have been embedded deeply within wall 800, grasping it. Because actuator 811 may comprise a variety of devices, many of which may have recoil, grasping claws 721 aid in preventing missile 701 from backing out of wall 800 in the event of that recoil. Blocks 715 also may aid in preventing movement from recoil by resisting reverse movement within wall 800. A person within the target room penetrated may also be prevented from shoving missile 701 back out of the room, for these same reasons.

Figure 9:
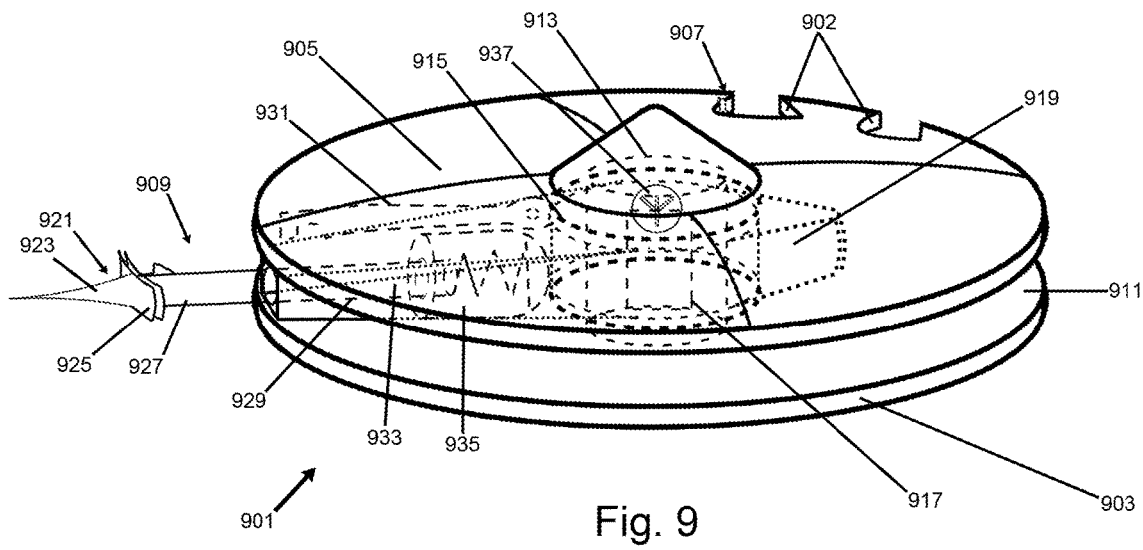
FIG. 9 is a perspective view depicting an exemplary trace evidence-creating and recovering projectile, in accordance with aspects of the present invention.

FIG. 9 is a perspective view depicting an exemplary trace evidence-creating and -recovering projectile 901, in accordance with aspects of the present invention. A streamlined, generally disk-shaped outer housing 903 with a convex upper fairing or streamlining panel(s) 905 aids in developing lift and encouraging flight when projectile 901 is launched. In some embodiments, projectile 901 may be launched with a lateral spin by a launcher or by hand, to further aid in flight stability. If launched by a launcher, such as gun 1000, discussed below, holding tabs for engaging with a launching arm to create spin by pushing against them, such as examples 902, may be included, which may double as trace evidence gathering barbs—the rotating action of the disk leading to pulling and stowing surface materials from any object colliding with projectile 901. Specialized sub-barbs, such as exemplary sub-barb 907, may be included, to further encourage grabbing and stowing trace evidence. Although the example of a disk-shaped projectile is provided, it should be understood that a wide variety of projectile shapes, such as, but not limited to, spherical or bullet-shaped projectiles, may also, or alternatively, be used in conjunction with other aspects of the invention set forth below.

In some methods of use, projectile 901 is launched at a suspect in a crime scene and, preferably, at a suspect presenting a flight risk. Even more preferably, projectile 901 is fired at a part of the suspect's body having a low risk for serious injury, such as the flank, leg or arms, at a bare skin location or a location with little or thin clothing, to aid other aspects of the invention in gathering identifying information, such as tissue-bearing UNA, without causing permanent injury. Upon such a collision between projectile 901 and such a part of the suspect's body, a trace evidence extractor device 909, within projectile 901, will turn to face that part of the suspect's body. To accomplish this, extractor device 909 may be mounted and swivel within a slot 911 of projectile 901, and is preferably mounted on a turnable vertical axel 913, which is itself mounted in the housing 903, at the center of projectile 901. In some embodiments, a motor 915, controlled by a local control unit 917 with which it is electronically connected or otherwise able to communicate, may drive and control axel 913 and extractor device 909. Sensors (not pictured) comprised in or connected to control unit 917, and such as accelerometers, may indicate to control unit 917 when a collision has occurred and, if so, the direction (or average or other function of direction) of acceleration resulting from that collision. Following this, the control system may direct extractor device 909 to turn and face the opposing direction of that deceleration, indicating the direction of the object with which projectile 901 has collided. Without a motor and control system, extractor device 909 will naturally turn in approximately this same direction if it is weighted slightly more than any opposing counterweight, such as exemplary counterweight 919, on the other side of axel 913. In either event, once extractor device 909 has swiveled to point at the body/object with which projectile 901 has collided, control unit 917 may next drive a linear actuator (such as releasable spring unit 919) to drive a secondary extractor projectile 921 outward (as pictured) and into the body/object. Extractor projectile 921 may comprise a tissue- or fluid-extracting hypodermic needle 923, or any other device for grabbing, pulling, stowing or recording trace (or, in some embodiments, other) evidence, such as but not limited to hooks, burrs, adhesives, and projections. Extractor projectile 921 preferably also comprises at least one repulsion bumper 925. In one embodiment, extractor projectile 921 comprises a telescoping rod 927, ejected partly from a barrel 929 (as pictured) when control unit 917 releases a pivoting releasable notched holding arm 931. When not yet released, secondary extractor projectile 921 preferably fits entirely, and may be freely swiveled, within slot 911. Thus, control unit 917 can withhold or launch extractor projectile 921 by allowing actuating spring 919 to push and eject it (as pictured). Rod 927 preferably comprises a hollow core 933, which opens onto both hypodermic needle 923 and a storage tank 935, with negative pressure. This negative pressure can be encouraged by the ejection of rod 927, if properly sealed as it telescopes, because the combined volume of core 933 and tank 935 resultantly increases, creating a sealed vacuum. Thus, when projectile 901 collides with a suspect at which it was fired, extractor projectile 921 is released at and pushed into the suspect's body, piercing clothing and the skin at the point of collision, creating a suction to extract a tissue or fluid which fills tank 935. Bumper 925, being more flush to the surface of the suspect's body, does not pierce but rather pushes against it which action, in turn, launches all of projectile 901 away from the suspect's body. The distance that projectile 901 is launched away from the suspect's body by the release of secondary projectile 921 from projectile 901 is preferably sufficiently great to prevent a suspect from readily grabbing it (e.g., 3 feet or a meter away, and preferably a much greater distance). Projectile 901 may be physically tethered or locatable and identifiable through unique marking and communications capabilities. In some embodiments, control unit 917 comprises communications hardware, such as a radio and antenna 937. Thus, using an external control unit, such as the control system set forth above in FIG. 5, a user may locate projectile (e.g., using G.P.S. location hardware and a beacon within control unit 917). In the event that a suspect does somehow find and retain projectile 901, these location aspects aid in locating the suspect, who is thereby carrying a beacon. The location beacon is preferably protected from tampering with a hardened case and may also comprise an alarm. Projectile 901 may also comprise surface covering trace evidence barbs and extractors, such as barb 907 but more numerous and uniformly-covering, making any handling by the suspect result in further evidence gathering.

An exemplary usage sequence, in accordance with the functionality set forth above, is discussed in greater detail below, with reference to FIG. 10.

Figure 10:
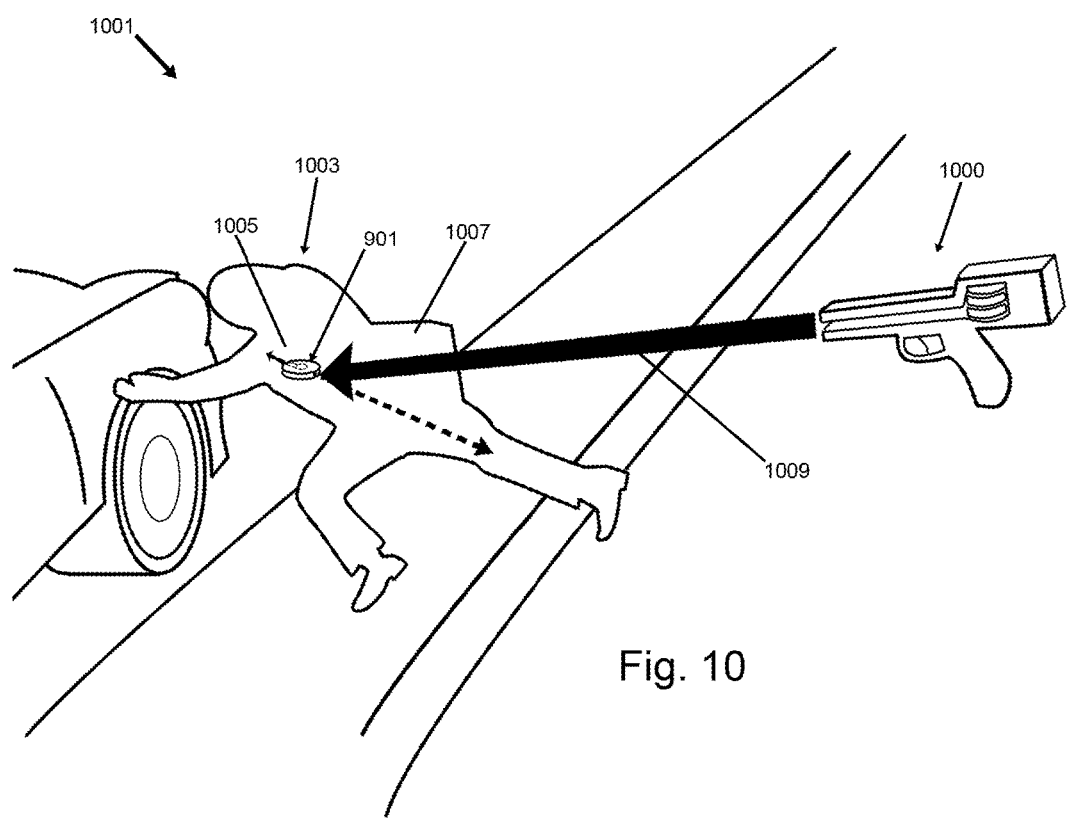
FIG. 10 is a perspective view of an exemplary crime scene, in which the exemplary trace evidence-creating and -recovering projectile of FIG. 9 is deployed by a specialized gun.

FIG. 10 is a perspective view of an exemplary crime scene 1001, in which the exemplary trace evidence-creating and -recovering projectile 901 of FIG. 9 is deployed by a specialized gun 1000. In crime scene 1001, a suspect 1003 is fleeing an area in which he or she has committed a crime, such as robbery. A user (not pictured) of gun 1000, and the system comprising gun 1000 and projectile 901, has aimed gun 1000 at a part of suspect 1003's body unlikely to cause any permanent physical injury—namely, suspect 1003's rear shoulder 1005. The user has aimed gun 1000 away from a parcel 1007, carried on his or her back, to avoid damaging it and to harvest more useful trace evidence. Unlike the area of suspect 1003's back covered by parcel 1007, the shoulder 1005 is covered only by one, two or three layers of clothing, each of which, and together, are insufficient to prevent projectile 921 and needle 923 from penetrating through to pierce suspect 1003's skin. The user proceeds to launch projectile 901, along the path indicated by trajectory arrow 1009, into suspect 1003's shoulder 1005.

As discussed above, upon colliding with the suspect's shoulder, evidence extractor device 909, either by collision forces or by active actuation, swivels to face suspect 1003. The control system governing device 909 then may lock it in place rotationally, through motor 915, and then launch a secondary extractor projectile 921, into the suspect's shoulder, extracting DNA and/or other trace forensic evidence. In some embodiments, device 909 may also implant a trackable tag into the suspect, such as a GPS locator or passively locatable tag. As also discussed above, the force of launching secondary projectile 921 causes a repulsive force, effective after (and only after) extracting tissue, blood, or other fluids from suspect 1003. First, secondary projectile 921 delivers a pushing force, indicated by secondary projectile force arrow 1011, into the shoulder 1005. The normal forces of the shoulder will then cause acceleration, and a new, ejecting flight path, as illustrated by force and flight path indicating arrow 1013. Projectile 901 is thereby ejected from the user's shoulder, and downward with gravity, to a location on the ground several feet from suspect 1003.

Even if suspect 1003 then is able to flee crime scene 1001, for example, by entering motor vehicle 1015 and driving away, projectile 901 can then be recovered by the user, or law enforcement personnel, and the suspect 1003's DNA, or other trace evidence related to suspect 1003, can be extracted from projectile 901 for laboratory and legal analysis.

To aid in establishing chain of custody, and in tying projectile 901 with the suspect's behavior and crime scene, gun 1000 may itself comprise a camera (not pictured), preferably trained in the direction in which gun 1000 is aimed, but with a lens or lenses covering at least 180 degrees (and preferably more). Gun 1000 also preferably comprises a control system, such as the control system set forth above in reference to FIG. 5, GPS hardware and wireless communications hardware, such that a timestamp, geolocation, all footage, and other crime-scene-related data generated by the system may be immediately and verifiably recorded on remote servers, as well as on a local data storage unit.

Gun 1000 may comprise any form of projectile launching apparatus and storage device appropriate to the application of launching projectiles, such as, but not limited to, firearm mechanisms, spring-gun mechanisms, disk-launchers and electromagnetic accelerators (in which case, disk 901 would be ferromagnetic and preferably magnetized at launch). As pictured, gun 1000 may comprise a feeding storage magazine, such that several projectiles, such as projectile 901, may be fired in rapid succession from gun 1000 toward a suspect or suspects.

Figure 11:
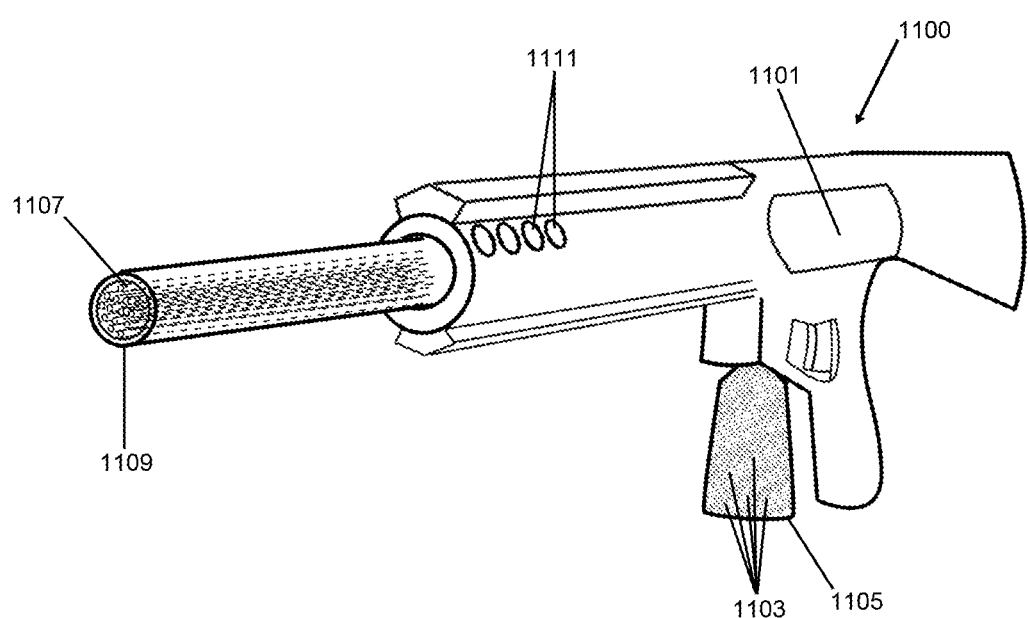
FIG. 11 is a perspective drawing of an exemplary electromagnetic accelerator gun, in accordance with aspects of the present invention.

FIG. 11 is a perspective drawing of an exemplary electromagnetic accelerator gun 1100, in accordance with aspects of the present invention. As with other rail guns, gun 1100 comprises an electromagnetic pulsing unit 1101, held within the body of gun 1100. Pulsing unit 1101 charges rails 1107 within a barrel 1109, to accelerate an armature projectile, such as particles 1103, shown within a funneling and feeding mechanism 1105. However, unlike conventional rail guns, rails 1107 are far more than two in number, having an opposing charge with other, neighboring rails at the time when an armature/particle is accelerated between any of them, simultaneously or in rapid succession. Thus, each rail 1107 is individually chargeable, by a control system, such as the control system set forth above in reference to FIG. 5. As with other rail guns, the speeds that can be reached by particles/armatures exiting barrel 1109 can exceed many times the speed of sound. Thus, when exiting barrel 1109 in a steady stream, which need not be literally simultaneous, and with sufficient energy, the effect may be a steady stream or ray of such particles, covering a wider area than the profile of each individual particle, creating the effect of an energetic beam, rather than a succession of individual shots.

Figure 12:
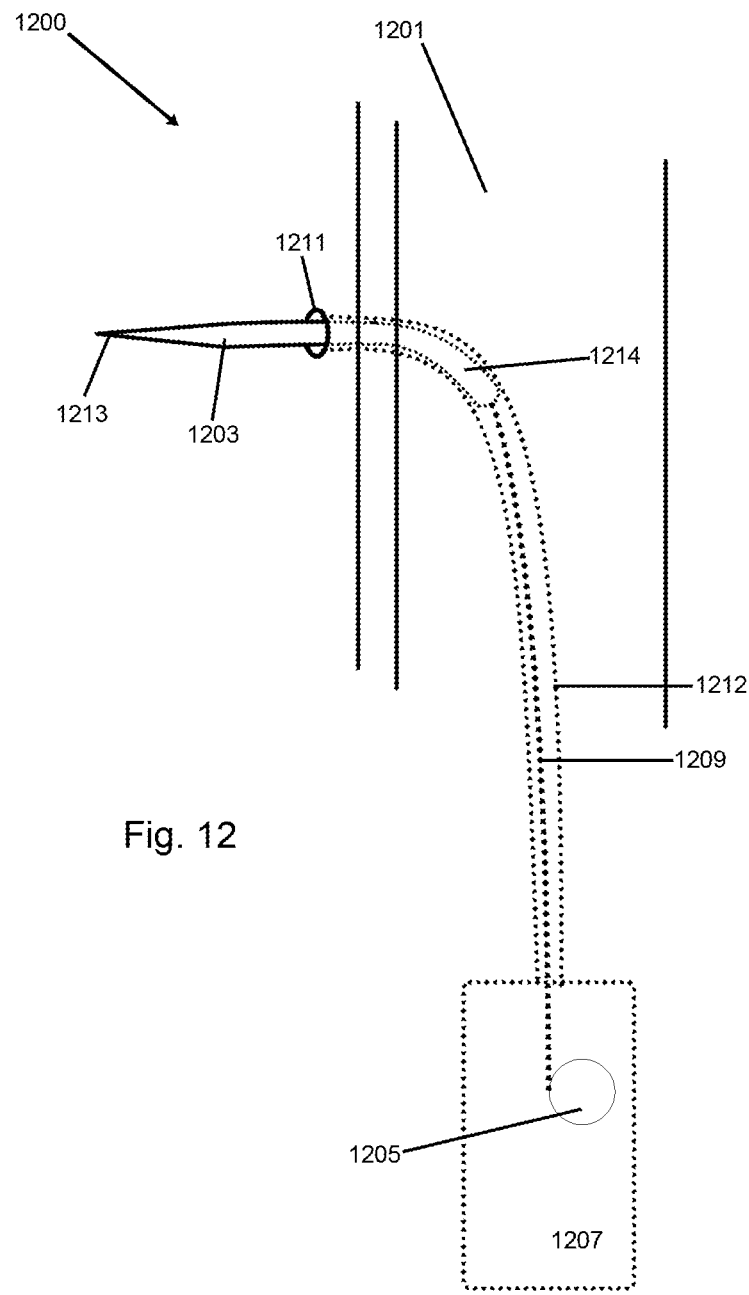
FIG. 12 is a side view of an exemplary trace evidence-creating and -recovering projectile launching and recovering device mounted in a wall, in accordance with aspects of the present invention.

FIG. 12 is a side view of an exemplary trace evidence-creating and -recovering projectile launching and recovering device 1200 mounted in a wall 1201, in accordance with aspects of the present invention. Device 1200 comprises a projectile 1203, similar in nature and design to the trace evidence-creating and -recovering projectiles set forth above. However, rather than being mounted on a swivel, or being launched completely away from a launcher, projectile 1203 is tethered to a motor 1205, held at the base of the device within a recovery safe 1207, within wall 1201. The tether 1209 is variably wound around rotary motor 1205 and, because it is made of a semi-stiff but turnable material (such as nylon), it may be used to retract projectile 1203, or advance it outward, through exit 1211 via guide channel 1212, to gather trace evidence as described above with reference to other projectiles. As with the other projectiles set forth above, projectile 1203 may comprise a hypodermic needle 1213, and vacuum reservoir 1214, or any other suitable trace evidence gathering sub-device.

Device 1200 preferably is used in conjunction with a building alarm or security system, and a control unit, such as the control unit set forth above in reference to FIG. 5. When the security system is armed, a sensor, such as a camera or IR sensor at or about exit 1211, and also embedded in wall 1201, can detect if an intruder is abutting exit 1211 and, if so, the control system can command motor 1205 to extend projectile 1203 out of exit 1211, piercing the intruders clothing and skin and extracting trace evidence and/or placing a tag, as discussed for other such projectiles above.

I claim:

1. An evidence collection system, comprising a projectile with: an extraction device configured to obtain identifying evidence and hold it wherein said extraction device is configured to obtain identifying evidence upon collision with person, animal or object; wherein said projectile is configured to be launched through a projectile guide installed within a building wall; and wherein said projectile is configured to be retracted into said wall.

2. The evidence collection system of claim 1, wherein said system comprises a launcher configured to launch said projectile.

3. The evidence collection system of claim 2, wherein said launcher comprises a camera.

4. The evidence collection system of claim 2, wherein said launcher comprises a control system comprising computer hardware.

5. The evidence collection system of claim 4, wherein said control system is configured to provide a time stamp and location associated with a launching event.

6. The evidence collection system of claim 1, wherein said system comprises a camera.

7. The evidence collection system of claim 1, comprising a control system comprising computer hardware.

8. The evidence collection system of claim 7, wherein said control system is configured to provide a time stamp and location associated with a launching event.

9. The evidence collection system of claim 1, wherein a tether is attached to said projectile.

10. The evidence collection system of claim 1, wherein said projectile implants a tag into said person, animal or object upon said collision.

11. The evidence collection system of claim 1, wherein said system comprises an alarm.

12. The evidence collection system of claim 1, comprising a protective case or other armor configured to prevent access to said projectile.

13. The evidence collection system of claim 1, wherein said projectile comprises barbs, hooks, adhesives, projections or other surface features configured for creating trace evidence upon said collision.

14. A method for deploying a projectile, comprising the following steps: launching said projectile at a person, animal or object; wherein said projectile comprises: an extraction device configured to obtain identifying evidence and hold it; wherein said extraction device is configured to obtain identifying evidence upon collision with a person, animal or object; wherein said projectile is configured to be launched through a projectile guide installed within a building wall; and wherein said projectile is configured to be retracted into said wall.

15. The method for deploying a projectile of claim 14, wherein a system comprises a launcher configured to launch said projectile.

16. The method for deploying a projectile of claim 15, wherein said launcher comprises a projectile guide installed within a building wall.

17. The method for deploying a projectile of claim 15, wherein said launcher comprises a camera.

18. The method for deploying a projectile of claim 15, wherein said system comprises a control system comprising computer hardware.

19. The method for deploying a projectile of claim 18, wherein said control system is configured to provide a time stamp and location associated with a launching event.

20. The method for deploying a projectile of claim 14, wherein a tether is attached to said projectile.

* * * * *